US011305006B2

(12) United States Patent
Chen et al.

(10) Patent No.: US 11,305,006 B2
(45) Date of Patent: Apr. 19, 2022

(54) AVIAN INFLUENZA AND FOWL ADENOVIRUS TYPE 4 BI-COMBINED GENETIC ENGINEERING SUBUNIT VACCINE AND METHOD FOR PREPARING THE SAME

(71) Applicants: ZHAOQING DAHUANONG BIOLOGY MEDICINE CO., LTD, Zhaoqing (CN); ZHAOQING INSTITUTE OF BIOTECHNOLOGY CO., LTD, Zhaoqing (CN)

(72) Inventors: Ruiai Chen, Zhaoqing (CN); Yanpeng Li, Zhaoqing (CN); Lianghai Wen, Zhaoqing (CN); Wenyan Zhang, Zhaoqing (CN); Jianjun Sun, Zhaoqing (CN)

(73) Assignees: ZHAOQING DAHUANONG BIOLOGY MEDICINE CO., LTD, Zhaoqing (CN); ZHAOQING INSTITUTE OF BIOTECHNOLOGY CO., LTD, Zhaoqing (CN)

(*) Notice: Subject to any disclaimer, the term of this patent is extended or adjusted under 35 U.S.C. 154(b) by 0 days.

(21) Appl. No.: 17/473,972

(22) Filed: Sep. 13, 2021

(65) Prior Publication Data
US 2022/0047693 A1   Feb. 17, 2022

Related U.S. Application Data

(63) Continuation of application No. PCT/CN2019/085075, filed on Apr. 29, 2019.

(30) Foreign Application Priority Data

Apr. 22, 2019 (CN) .......................... 201910321818.6

(51) Int. Cl.
| | | |
|---|---|---|
| *A61K 39/145* | (2006.01) | |
| *A61P 31/16* | (2006.01) | |
| *A61K 39/235* | (2006.01) | |
| *C12N 7/00* | (2006.01) | |

(52) U.S. Cl.
CPC .......... *A61K 39/145* (2013.01); *A61K 39/235* (2013.01); *A61P 31/16* (2018.01); *C12N 7/00* (2013.01)

(58) Field of Classification Search
None
See application file for complete search history.

(56) References Cited

U.S. PATENT DOCUMENTS 7,504,120 B2 *   3/2009   Steer ..................... C12N 9/248
                                                    426/63
8,784,819 B2     7/2014   Yusibov et al.

FOREIGN PATENT DOCUMENTS

| CN | 105582533   | * | 5/2016 |
| CN | 105582533 A |   | 5/2016 |

OTHER PUBLICATIONS

Ruan et al. Inf, Gen, and Evol. vol 61 pp. 145-150 (Year: 2018).*
Internation Search Report of PCT/CN2018/080591, dated Mar. 27, 2018.
Chu, Dianfeng et al., "Research Progress on the Vaccine Against Fowl Adenovirus Group I ", China Poultry vol. 39, No. 12, Jun. 30, 2017, pp. 44-47.
Xie Q. et al., "Preparation and immune activity analysis of H5N1 subtype avian influenza virus recombinant protein-based vaccine", Poult Sci., vol. 88, No. 8, Aug. 31, 2009, pp. 1608-1615.

* cited by examiner

*Primary Examiner* — Shanon A. Foley
*Assistant Examiner* — Myron G Hill

(57) ABSTRACT

The disclosure relates to the technical field of veterinary biological products, and discloses an avian influenza and fowl adenovirus type 4 bi-combined genetic engineering subunit vaccine. An antigen in the vaccine is a fusion antigen; the fusion antigen has a) avian influenza virus HA protein; b) fowl adenovirus fiber2 protein; c) a specific linker peptide located between the avian influenza virus HA protein and the fowl adenovirus fiber2 protein; the amino acid sequence of the specific linker peptide is as shown in SEQ ID NO:2. This vaccine contains the fusion antigen which can induce poultries to produce a high-level specific antibody to protect poultries from avian influenza and fowl adenovirus infection. Meanwhile, the disclosure also discloses a method for preparing the vaccine.

10 Claims, 1 Drawing Sheet
Specification includes a Sequence Listing.

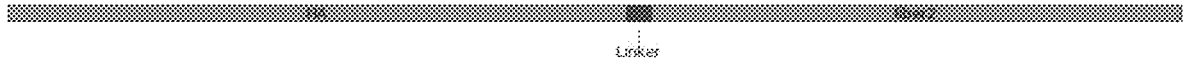

ized antibody neutralizing the infection of viruses.
AVIAN INFLUENZA AND FOWL ADENOVIRUS TYPE 4 BI-COMBINED GENETIC ENGINEERING SUBUNIT VACCINE AND METHOD FOR PREPARING THE SAME

CROSS-REFERENCE TO RELATED APPLICATIONS

This application is a continuation of International Patent Application No. PCT/CN2019/085075 with a filing date of Apr. 29, 2019, designating the United States, now pending, and further claims priority to Chinese Patent Application No. 201910321818.6 with a filing date of Apr. 22, 2019. The content of the aforementioned applications, including any intervening amendments thereto, are incorporated herein by reference.

INCORPORATION-BY-REFERENCE OF SEQUENCE LISTING

The Sequence listing, named "SEQUENCE LISTING", created by Nov. 2, 2021 with 14,855 size in bytes is incorporated by reference in this application.

TECHNICAL FIELD

The disclosure relates to the technical field of veterinary biological products, particularly to an avian influenza and fowl adenovirus type 4 bi-combined genetic engineering subunit vaccine and a method for preparing the same.

BACKGROUND OF THE DISCLOSURE

Avian influenza virus (AIV) is an important pathogen of a respiratory system for birds and some mammals, and belongs to orthomyxoviridae influenza virus in taxonomy. According to different protein antigenicities on the surface, the avian influenza virus is divided into 17 subtype hemagglutinins (HA) and 10 subtype neuraminidases (NA) in which H9N2 subtype avian influenza virus is widely epidemic all over the world, which can cause significant reduction in the egg yield of hens and decrease in feed reward, thereby leading to huge economic loss of poultry industry and bring about danger to human health. The pathogenesis of influenza virus on a host depends on multiple genes, wherein HA genes and proteins encoded by HA genes are extremely important, which play a crucial role in virus adsorption and transmembrane processes, are important surface antigens, stimulate an organism to generate a neutralizing antibody neutralizing the infection of viruses.

Fowl adenovirus (FAV) is distributed all over the world and has many serum types. The hydrocardia syndrome of broiler chickens caused by this virus is caused by fowl adenovirus-C' serum type 4 adenovirus infection. There are reports about this disease across the country. The morbidity of 3~5-week-old broiler chickens is particularly harmful, the mortality suddenly rises to over 80% when being serious, thereby seriously harming the healthy development of aviculture industry in China.

At present, prevention and control of vaccines is the most effective way for the above two diseases that are extremely harmful to poultry farming aviculture industry. However, in the prior art, a production process of preparing avian influenza vaccines using chick embryo breeding viruses relates to live virus operation which threatens the biological safety of the environment. In the meantime, when the avian influenza is epidemic, production of vaccines has the defects of long production period, low yield and the like due to limitation of chick embryo supply. The fowl adenovirus is not easy to culture, the virus having high titer is difficultly obtained, especially, different isolated strains have great difference, which results in a fact that the prepared vaccine often difficultly provides an ideal immune effect.

Based on the above problems, a selective means to solve the above problem is genetic engineering fermentation. The applicant, Qingdao Yibang Bioengineering Co., Ltd, applied patent application CN201710674039.5 in 2017, which discloses a newcastle disease, avian influenza, bursa fabricius and fowl adenovirus quadruple vaccine containing antigens and a vaccine adjuvant, wherein the antigens are a newcastle disease Lasota virus strain, H9 subtype avian influenza strain with conservation number CCTCCNO:V201517, a bursa fabricius VP2 Protein and an fowl adenovirus Hexon protein having an amino acid sequence of SEQ ID NO: 2 and a chicken $\alpha$-interferon protein.

Therefore, production of antigens based on genetic engineering fermentation is a biological technology which is widely being researched by those skilled in the art at present.

In the avian influenza and adenovirus bi-combined vaccine, the commonly used methods are to use avian influenza fluid and adenovirus fluid as a mixed antigen to produce the bi-combined vaccine, for example the applicant, Qingdao Yibang Bioengineering Co., Ltd, applied patent application CN201610099573.3 in 2016, which discloses a avian influenza virus and fowl adenovirus bi-combined inactivated vaccine. The H9 subtype avian influenza virus QDY strain used in the vaccine of the disclosure and TCID50/EID50 of I group 4 type fowl adenovirus YBAV-4 new strain are high in valence and good in immunogenicity, and can withstand attacks from isolated viruses of H9 subtype and fowl adenovirus diseases in different places. The vaccines prepared from the above viruses have good safety, and there are no any local and systemic adverse reactions caused by the vaccines. In storage life tests, through character and safety tests and analysis on potency test data, the results are compared with those of the single vaccine of the similar product, the bi-combined vaccine has no significant difference, they are both stable and effective; the results of the potency test prove that the bi-combined vaccine and two single vaccine antibodies are all maintained in high level, can quickly generate antibodies compared with the similar products, and the antibody in control group is negative.

However, the problems existing in the above solution are that there are many process steps of producing avian influenza viruses and adenoviruses alone; if the subunit vaccine is prepared based on the genetic engineering principle, how to screen effective antigenic determinants, especially screen two effective antigenic determinants at the same time, is still a problem, although the process steps can be simplified.

Further problem lies in that even though two or more effective antigenic determinants are screened, how to improve their exhibition effect in the subunit vaccine is a very difficult realistic problem.

SUMMARY OF DISCLOSURE

The objective of the disclosure is to provide an avian influenza and fowl adenovirus type 4 bi-combined genetic engineering subunit vaccine and a method for preparing the same. This vaccine contains a fusion protein which can induce poultries to generate high-level specific antibodies to protect the poultries from avian influenza and fowl adenovirus infection.

In order to achieve the above objective, the technical solution provided by the disclosure is to provide an avian influenza and fowl adenovirus type 4 bi-combined genetic engineering subunit vaccine, wherein an antigen in the vaccine is a fusion antigen; the fusion antigen has:

a) an avian influenza virus HA protein;
b) a fowl adenovirus fiber2 protein;
c) a specific linker peptide located between the avian influenza virus HA protein and the fowl adenovirus fiber2 protein; the amino acid sequence of the specific linker peptide is as shown in SEQ ID NO: 2.

The amino acid sequence of the specific linker peptide is as follows:

PEVLPPLPKESRISEGEAVVVG

In the above subunit vaccine, the amino acid sequence of the fusion antigen is as shown in SEQ ID NO: 3.

The amino acid sequence of the fusion antigen is as follows:

MEVVSLITILLVATVSNADKICIGYQSTNSTETVDTLTENNVPVTHAKE
LLHTEHNGMLCATSLGQPLILDTCTIEGLIYGNPSCDLSLEGREWSYIV
ERPSAVNGLCYPGNVENLEELRSLFSSARSYQRIQIFPDTIWNVSYDGT
STACSGSFYRSMRWLTRKNGDYPVQDAQYTNNQGKNILFMWGINHPPTD
TTQRNLYTRNDTTTSVATEEINRIFKPLIGPRPLVNGLMGRIDYYWSVL
RPSQTLRIKSDGNLIAPWYGHILSGESHGRILKTDLKRGSCTVQCQTEK
GGLNTTLPFQNVSKYAFGNCSKYIGIKSLKLAVGLRNVPSRSSRGLFGA
IAGFIEGGWSGLVAGWYGFQHSNDQGVGMAADRDSTQKAIDKITSKVNN
IVDKMNKQYEVIDHEFSEVETRLNMINNKIDDQIQDIWAYNAELLVLLE
NQKTLDEHDANVNNLYNKVKRALGSNAVEDGKGCFELYHKCDDQCMETI
RNGTYNRRKYQEESKLERQKIEGVKLESEGTYKILTIYSTVASSLVIAM
GFAAFLFWAMSNGSCRCNICI<u>PEVLPPLPKESRISEGEAVVVG</u>MLRAPK
RRHSENGKPETEAGPSPAPIKRAKRMVRASQLDLVYPFDYVADPVGGLN
PPFLGGSGPLVDQGGQLTLNVTDPIIIKNRSVDLAHDPSLDVNAQGQLA
VAVDPEGALDITPDGLDVKVDGVTVMVNDDWELAVKVDPSGGLDSTAGG
LGVSVDDTLLVDQGELGVHLNQQGPITADSSGIDLEINPNMFTVNTSTG
SGVLELNLKAQGGIQAASSGVGVSVDESLQIVNNTLEVKPDSGPLTVS
ANGLGLKYDTNTLAVTAGALTVVGGGSVSTPIATFVSGSPSLNTYNATT
VNSSANAFSCAYYLQQWNIQGLLVTSLYLKLDSATMGNRPGDLNSANAK
WFTFWVSAYLQQCNPSGIQAGTVSPSTATLTDFEPMANRSVTSPWTYSA
NGYYEPSIGEFQVFSPVVTGAWNPGNIGIRVLPVPVSASGERYTLLCYS
LQCTNASIFNPNNSGTMIVGPVLYSCPAASLP

In the above subunit vaccine, the content of the fusion antigen in the vaccine is not less than 75 µg/ml.

In the above subunit vaccine, the vaccine is formed by mixing and emulsifying an oil phase and a water phase; the water phase contains the fusion antigen.

Meanwhile, the discloses also discloses a method for preparing the avian influenza and fowl adenovirus type 4 bi-combined genetic engineering subunit vaccine as described above, wherein the vaccine is obtained by mixing and emulsifying the water phase containing the fusion antigen and the oil phase.

In the above method for preparing the subunit vaccine, the method for preparing the fusion antigen comprises:

Step 1: synthesizing a fusion expression gene sequence to construct a recombinant expression vector; synthesizing a fusion gene sequence shown in SEQ ID NO:1, and adding restriction enzyme sites ECOR I and NOT I at two ends of the fusion gene sequence, and meanwhile carrying out double digestion on *Pichia pastoris* expression vector pPic9k using the restriction enzymes ECOR I and NOT I to obtain a fragment with a size of 9263 bp, and linking the synthesized fusion gene sequence with the *Pichia pastoris* expression vector pPic9k fragment recovered after double digestion using 14 DNA ligase to obtain a ligation product;

the sequence of the fusion gene is as follows:

atggaagtagtatcactaataactatactactagtagcaacagtaagca
atgcagataaaatctgcatcggctatcaatcaacaaactccacagaaac
tgtggacacactaacagaaaacaatgtccctgtgacacatgccaaagaa
ctgctccacacagagcataatgggatgctgtgtgcaacaagcttgggac
aacctcttattttagacacctgcaccattgaagggctaatctatggcaa
tccttcttgtgatctatcgctggaaggaagagaatggtcctatatcgtc
gagagaccatcagctgtcaacggattgtgttaccccgggaatgtagaaa
atctagaagagctaaggtcactttttagttctgctaggtcttatcaaag
aatccagattttcccagacacaatctggaatgtgtcttacgatgggaca
agcacagcatgctcaggttcattctacgaagcatgagatggttgactc
gaaagaacggcgattaccctgtccaagacgcccaatacacaaataatca
agggaagaacattctttcatgtggggcataaatcacccacccaccgat
actacgcagagaaatctgtacacgagaaacgacacaacaacgagtgtgg
caacagaagaaataaataggatcttcaaaccattgataggaccaaggcc
tcttgtcaacggtttgatgggaagaattgattattattggtctgtattg
agaccgagtcaaacactgcgaataaaatctgatgggaatctaatagctc
catggtatggacacattctttcaggagagagccacggaagaattctgaa
gactgatttaaaaagggggtagctgcacagtgcaatgtcagacagagaaa
ggtggcttaaacacaacactgccattccaaaatgtaagtaagtatgcat
ttggaaactgctcaaaatacattggcataaagagtctcaaacttgcagt
tggtctgaggaatgtgccttctagatctagtagaggactattcggggcc
atagcagggtttatagagggaggttggtcagggctagttgctggttggt
atgggttccagcattcaaatgaccaaggggttggtatggcagcagatag
agactcaacccaaaaggcaattgataaaataacatccaaagtgaataat
atagtcgacaaaatgaacaagcagtatgaagtcattgatcatgaattca
gtgaggtagaaactagacttaacatgatcaataataagattgatgatca
aatccaggatatatgggcatataatgcagaattgctagttctgcttgaa
aaccagaaaacactcgatgagcatgacgcaaatgtaaacaatctatata
ataaagtaaagagggcgttgggttccaacgcggtggaagatgggaagg -continued

```
atgtttcgagctataccacaaatgtgatgaccaatgcatggagacaatt
cgaaacgggacctacaacagaaggaagtatcaagaggagtcaaaattag
aaagacagaaatagagggggtcaagctggaatctgaaggaacttacaa
aatcctcaccatttattcgactgttgcctcatctcttgtgattgcaatg
gggtttgctgccttcttgttctgggccatgtccaatgggtcttgcagat
gcaacatttgtatataacctgaagtcctgcctcctctgcctaaggaatc
tagaatttccgaaggtgaagctgtcgtcgtcggtatgctccgggcccct
aaaagaagacattccgaaaacgggaagcccgagaccgaagcgggacctt
ccccggctccaatcaagcgcgccaaacgcatggtgagagcatcccagct
tgacctggtttatcctttcgattacgtggccgaccccgtcggagggctc
aacccgccttttttgggaggctcaggaccccctagtggaccagggcggac
agcttacgctcaacgtcaccgatccatcatcatcaagaacagatcggt
ggacttggcccacgaccccagtctcgatgtcaacgcccaaggtcaactg
gcggtggccgttgaccccgaaggggccctggacatcaccccgatggac
tggacgtcaaggtcgacggagtgaccgtaatggtcaacgatgactggga
actggccgtaaaagtcgacccgtccggcggattggattccaccgcgggt
ggactgggggtcagcgtggacgacaccttgctcgtggatcagggagaac
tgggcgtacacctcaaccaacaaggacccatcactgccgatagcagtgg
tatcgacctcgagatcaatcctaacatgttcacggtcaacacctcgacc
ggaagcggagtgctggaactcaacctaaaagcgcagggaggcatccaag
ccgccagttcgggagtgggcgtttccgtggatgaaagcctacagattgt
caacaacactctggaagtgaaaccggatcccagcggaccgcttacggtc
tccgccaatggcctagggctgaagtacgacactaataccctagcggtga
ccgcgggcgctttaaccgtggtcggaggggggagcgtctccacaccat
cgctactttgtctcgggaagtcccagcctcaacacctacaatgccacg
accgtcaattccagcgcgaacgccttctcttgcgcctactaccttcaac
agtggaacatacaggggctccttgttacctccctctacttgaaattgga
cagcgccaccatggggaatcgcctggggacctcaactccgccaatgcc
aaatggttcacctttgggtgtccgcctatctccagcaatgcaaccccct
ccgggattcaagcgggaacggtcagcccctccaccgccaccctcacgga
ctttgaaccccatggccaataggagcgtgaccagcccatggacgtactcg
gccaatggatactatgaaccatccatcggggaattccaagtgttcagcc
cggtggtaacaggtgcctggaacccgggaaacatagggatccgcgtcct
ccccgtgccggtttcggcctccggagagcgatacaccttctatgctat
agtctgcagtgcacgaacgcgagcattttttaatccaaacaacagcggaa
ccatgatcgtgggacccgtgctctacagctgtccagcggcctccctccc
gtaa
```

The above underline part (SEQ ID NO: 4)
<u>cctgaagtcctgcctcctctgcctaaggaatctagaatttccgaaggt
gaagctgtcgtcgtcgg</u> is a gene position of a specific linker peptide fragment.

Step 2: transforming the ligation product in step 1 into *E. coli* DH5α, picking colonies, carrying out positive cloning verification using PCR, and carrying out sequencing verification on a target fragment;

The above target fragment refers to a linkage product, sequencing verification of the target fragment is to demonstrate whether the linkage product succeeds in transforming into *E. coli* DH5α;

Step 3: after sequencing in step 2 succeeds, extracting plasmids from the colonies to obtain recombinant plasmids, introducing the recombinant plasmids into *Pichia pastoris* GS11 using an electrotransformation method to obtain thallus;

The above recombinant plasmid refers to the linkage product.

Step 4: collecting the thallus in step 3 and picking transformants capable of normally growing on a resistance plate, extracting genomes from the transformants, and carrying out PCR amplification on the target fragment;

The above transformant is a normally grown bacterium obtained by screening the thallus transformed in Step 3 on the plate of the YPD solid culture medium containing G418 antibiotics.

The target fragment in Step 4 refers to the linkage product, the target fragment contained in a genome undergoes PCR amplification, the existence of the target fragment is verified, if yes, Step 5 is conducted.

Step 5: after the target fragment is determined, activating the transformants again, and carrying out fermentation induction culture to obtain a protein solution containing the fusion antigen; and Step 6: purifying and precipitating the protein solution to obtain the fusion antigen.

In the above method for preparing the subunit vaccine, the Step 2 is specifically as follows: the ligation product in step 1 is transformed into *E. coli* DH5 α, 100 μl of *E. coli* DH5α cells molten on ice is put into a 5 ml EP tube with a round bottom, the ligation product in step 1 is added, the resulting mixture is put for 30 s on ice, subjected to heat shock for 45 s at 42° C., and then put on ice for 1-2 min, an soc culture medium is added until the final volume is 1 ml, the resulting mixture is subjected to shaking culture at 37° C. for 1 h, and a proper amount of cultured product is coated on an LB agar plate and cultured overnight at 37° C.; colonies are picked to be subjected to positive cloning verification using PCR, and sequencing verification is performed on the target fragment;

the step 3 is specifically as follows: after sequencing succeeds, plasmids are extracted from the colonies to obtain the recombinant plasmids, the recombinant plasmids are introduced into *Pichia pastoris* GS11 by using an electrotransformation method, wherein the electrotransformation conditions are as follows: the prepared recombinant plasmids are added into a 1.5 mL centrifuge tube containing 80 μL of *Pichia pastoris* GS115 competent cells to be subjected to ice bath for 15 min to obtain a plasmid competent mixed solution, the sucked plasmid competent mixed solution is added into a pre-cooled 0.2 cm electroconversion cup and the cup is subjected to electric shock transformation on an electromotor; electric shock is performed for 4.5 ms at 1500 V; after electric shock is completed, 500 μL of 1M pre-cooled sorbitol solution is added immediately and evenly mixed, the resulting mixed solution is transferred into a 1.5 mL centrifuge tube, and cultured for 2 h in a constant temperature shaker at 30° C. at 180 rpm; the resuscitated bacterial solution was centrifuged at a low speed for 5 min and 150-200 μL of suspended thallus is retained and coated on an YPD plate containing 1 M sorbitol and cultured for 48 h in a constant temperature incubator at 30° C.

In the above method for preparing the subunit vaccine, the step 4 is specifically as follows: the thallus on the YPD plate in step 3 are collected and diluted into corresponding folds, 150-200 μL of bacterial solution is sucked to the YPD culture medium containing 0.4 g/ml G418 antibiotics, and statically cultured in a 30° C. constant temperature incubator for 2-4 days, transformants capable of normally growing on the resistance plate are picked to extract the transformant genome, and PCR amplification is performed on the target fragment.

In the above method for preparing the subunit vaccine, the step 5 is specifically as follows: the verified transformants are picked and inoculated in a BMGY culture solution to be subjected to shaking culture for 48 h at 30° C., then the cultured product is centrifuged under a low temperature at 4000 rpm for 10 min to remove the supernatant, then the BMMY culture solution are added to suspend the thallus, then the thallus is induced for 72 h with addition of methanol every 24 h; the culture solution was centrifuged under a low temperature at 4000 rpm for 10 min, and the supernatant is collected to obtain a protein solution, and SDS-PAGE identification is performed on the protein solution;

the step 6 is specifically as follows: absolute ethanol whose volume is as twice as that of protein solution is added overnight for settlement, the solution after settlement is centrifuged under a low temperature at 8000 rpm/min for 5 min to remove the supernatant, and the avian influenza H9 subtype HA and adenovirus type 4 fiber2 fusion antigen is collected and precipitated.

In the above method for preparing the subunit vaccine, the emulsifier used in the oil phase is span-80 and the solvent is white oil;

the emulsifier used in the water phase is Tween 80 and the solvent is water.

The disclosure has the beneficial effects:

The vaccine of the disclosure adopts the fusion antigen, which has the advantages:

1. The fusion antigen can induce poultries to produce high-level specific antibodies and protect poultry from avian influenza and fowl adenovirus infection;

2. The specific linker peptide is added between avian influenza virus HA and fowl adenovirus fiber2 to assist in the fusion expression of avian influenza virus HA and fowl adenovirus fiber2 and optimize the folding of fusion protein molecules;

3. The avian influenza virus HA protein and fowl adenovirus fiber2 protein are fused in series and expressed for the first time, so as to reduce the repetitive works in the actual production and increase labor efficiency.

The method for preparing the fusion antigen in the vaccine of the disclosure is genetic engineering fermentation. The method has the advantages of low cost, high antigen purity, good immunogenicity and high safety.

DESCRIPTION OF THE DRAWINGS

FIG. 1 is a structural diagram of a fusion gene sequence of example 1 of the disclosure.

DETAILED DESCRIPTION OF PREFERRED EMBODIMENTS

Next, the disclosure will be described in combination with specific embodiments, but it is understood that these specific embodiments are only for illustrating the disclosure but not limiting the disclosure. Those skilled in the art can make improvements to specific embodiments or technical features of the disclosure under the enlightenment of the disclosure, but those improved or substituted technical solutions are still included within the protective scope of the disclosure.

Example 1

Preparation of a fusion antigen based on avian influenza virus HA protein and fowl adenovirus fiber2 protein:

Raw materials: *Pichia pastoris* GS115 and pPic9K plasmids were provided by the research group of Han Nanyu, School of life sciences, Yunnan Normal University; The above raw materials are also commercially available commodities, such as *Pichia pastoris* GS115 (production company: Invitrogen™; strain type: *Pichia pastoris*; catalog No.: C181-00; culture medium: YPD culture medium; growth conditions: 28-30° C., aerobic; genotype: His4; phenotype: Mut$^+$; plasmid transformation conditions: electrotransformation; application: protein expression; induction method: methanol); pPic9K plasmid (produced by Invitrogen™; product name: pPIC9K *Pichia* vector; article No.: V17520)

*E. coli* DH5 α, plasmid extraction kit and restriction enzyme were purchased from TaKaRa-Bao Bioengineering (Dalian) Co., Ltd; T4 DNA ligase is a T4 DNA ligase, which is a commercially available product.

The components of a bacterial/fungal culture medium and antibiotics such as geneticin G-418 were purchased from bioengineering Shanghai (Co., Ltd.), and the full-length fusion gene was synthesized by bioengineering Shanghai (Co., Ltd.).

The following steps are included:

Step 1: a fusion expression gene sequence was synthesized and a recombinant expression vector was constructed; a fusion gene sequence was synthesized (synthesized by Sangong bioengineering Shanghai Co., Ltd.), and the restriction enzyme sites ECOR I and NOT I were added at two ends of the fusion gene sequence, and meanwhile double digestion was carried out on a *Pichia pastoris* expression vector pPic9k using the restriction enzymes ECOR I and NOT I to obtain a fragment with a size of 9263 bp, and the synthesized fusion gene sequence was linked with the *Pichia pastoris* expression vector pPic9k fragment recovered via double digestion using T4 DNA ligase to obtain a ligation product. The sequence of the fusion gene is as shown in FIG. 1, the avian influenza H9 subtype HA gene and the adenovirus type 4 fiber2 gene are located at two ends in FIG. 1, which are linked using a specific linker peptide fragment gene.

Step 2: the ligation product in step 1 was transformed into *E. coli* DH5α, the specific steps are as follows: 100 μl of *E. coli* DH5α cells molten on ice is put into a 5 ml EP tube with a round bottom, the ligation product (<10 ng) in step 1 was added, the resulting mixture was put for 30 s on ice, subjected to heat shock for 45 s at 42° C., and then put on ice for 1-2 min, an soc culture medium was added until the final volume was 1 ml, the resulting mixture was subjected to shaking culture at 37° C. for 1 h, and a proper amount of cultured product was coated on an LB agar plate and cultured overnight at 37° C.; colonies were picked to be subjected to positive cloning verification using PCR, and sequencing verification was performed on the target fragment;

Step 3: after sequencing succeeds, plasmids were extracted to obtain recombinant plasmids, the recombinant plasmids were introduced into *Pichia pastoris* GS11 using an electrotransformation method, the electrotransformation conditions were as follows: the prepared recombinant plasmids were added into a 1.5 mL centrifuge tube containing 80 μL of *Pichia pastoris* GS115 competent cells to be subjected to ice bath for 15 min to obtain a plasmid competent mixed solution, the sucked plasmid competent mixed solution was added into a pre-cooled 0.2 cm electroconversion cup and the cup was subjected to electric shock transformation on an electromotor; electric shock was performed for 4.5 ms at 1500 V; after electric shock was completed, 500 μL of 1M pre-cooled sorbitol solution was added immediately and evenly mixed, the resulting mixed solution was transferred into a 1.5 mL centrifuge tube, and cultured for 2 h in a constant temperature shaker at 30° C. at 180 rpm; the resuscitated bacterial solution was centrifuged at a low speed for 5 min and 150-200 μL of suspended thallus is retained and coated on an YPD plate containing 1 M sorbitol and cultured for 48 h in a constant temperature incubator at 30° C.;

Step 4: screening transformants by resistance concentration gradient;

transformants were screened from *Pichia pastoris* GS11 in which recombinant plasmids were introduced in Step 3 using resistance concentration gradient, the transformants containing the recombinant plasmids were screened on YPD plates having geneticin G-418 resistance concentrations of 0.2 and 4 mg/ml respectively, the transformants capable of normally growing on the high-concentration resistance plate were picked, transformant genomes were extracted, and PCR amplification was performed on the target fragment;

Step 5: after the target fragment was determined, the transformants were activated again, fermentation induction culture was performed to obtain a protein solution containing the fusion antigen;

the verified transformants were picked and inoculated into a BMGY culture medium to be subjected to shaking culture for 48 h at 30° C., then the cultured product is centrifuged under a low temperature at 4000 rpm for 10 min to remove the supernatant, then the BMMY culture solution were added to suspend the thallus, then the thallus was induced for 72 h with addition of methanol every 24 h; the culture solution was centrifuged under a low temperature at 4000 rpm for 10 min, and the supernatant was collected to obtain a protein solution, and SD S-PAGE identification was performed on the protein solution;

Step 6: the protein solution was purified and precipitated. Absolute ethanol whose volume was as twice as that of protein solution was added overnight for settlement, the solution after settlement was centrifuged under a low temperature at 8000 rpm/min for 5 min to remove the supernatant, and the avian influenza H9 subtype HA and adenovirus type 4 fiber2 fusion antigen was collected.

Example 2

The preparation of the bi-combined genetic engineering subunit vaccine of avian influenza and fowl adenovirus type 4 comprises the following steps:

(1) preparation of an oil phase: 94 weight parts of injected white oil and 6 weight parts of Span-80 were mixed to prepare the oil phase, the oil phase was sterilized at 121° C. for 30 min, and cooled to room temperature for later use;

(2) preparation of a water phase: the fusion antigen prepared in example 1 was diluted into to 96 weight parts so that the content of the fusion antigen in the vaccine was 75 μg/ml, 4 weight parts of Tween-80 after sterilization and cooling were added, and the above substances were fully stirred until being completely dissolved;

(3) emulsification: 3 weight parts of oil phase was poured into an emulsifying tank to be mixed, then 2 parts of water phase was slowly added, and the above substances were emulsified for 60 min at the emulsification speed of 2000 r/min; and (4) subpackaging: the obtained product was subjected to aseptic quantitative subpackaging, sealed with a cover and stored at 2-8° C.

After extensive experimental verification, as long as the content of the fusion antigen is not less than 75 μg/ml and the emulsion system can meet the emulsion and stabilization requirements required by the vaccine, all the vaccines can achieve the effect of the following vaccine immune efficacy experiments. Therefore, the amounts of the emulsifier and the oil in the oil phase and the amounts of the emulsifier and the oil in the water phase are all not emphasized by the disclosure, and any ordinary vaccine emulsifying formula is applicable to the disclosure.

Example 3

Vaccine Immune Efficacy Test (1) Immune Protection Against Avian Influenza (H9 subtype)

15 28-day-old SPF chickens were used, among them, 10 chickens were injected subcutaneously with 0.3 ml of avian influenza and fowl adenovirus type 4 bi-combined genetic engineering subunit vaccine (example 2) in the neck, and another 5 chickens were used as avian influenza challenge control. On the d21 after inoculation, each chicken was intravenously injected with 0.2 ml of H9 subtype avian influenza virus DA strain chicken embryo virus (containing× $10^{7.0}EID_{50}$). On the d5 after challenge, cotton swabs were collected from the throat and cloaca of each chicken, their supernatants were mixed and then embryos of 5 9~11-day-old SPF chickens were inoculated via allantoic cavity for 0.2 ml per embryo, incubated and observed for 72 h, and the HA titers of all chicken embryo fluids were measured. Among the 5 chicken embryos inoculated in each mixed swab sample, as long as the HA titer of the chicken embryo fluid of 1 chicken embryo is not less than 1:16, the sample can be determined as positive virus isolation. The samples with negative virus isolation should be determined after passage for one generation.

The results show that 10 immunized chickens exhibit negative virus isolation and 5 control chickens exhibit positive virus isolation.

(2) Immune Protection Against Fowl Adenovirus Type 4

15 21-day-old SPF chickens were used, among them, 10 chickens were injected subcutaneously with 0.3 ml of avian influenza and fowl adenovirus type 4 bi-combined genetic engineering subunit vaccine (example 2) in the neck, and another 5 chickens were used as fowl adenovirus type 4 challenge control. On the d21 after inoculation, both of immune group and control group were intramuscularly injected with fowl adenovirus type 4 isolate GX-1 strain (NCBI register number: MH454598, and the content of viruses was not less than $10^{6.0}TCID_{50}$/ml, 0.3 ml for each chicken. The morbidity and mortality of animals were observed after challenge.

The results show that all the 10 immunized chickens can resist the attack of fowl adenovirus type 4 isolate GX-1 strain, and survive without diseases and death; All 5 animals in the control group are died due to morbidity.

In the disclosure, the HA protein of avian influenza virus and fowl adenovirus fiber2 protein are fused in series for the first time to prepare the vaccine, so as to reduce the repetitive work in actual production and increase labor efficiency.

Addition of the specific linker peptide is added between avian influenza virus HA and fowl adenovirus fiber2 assists in the fusion expression of avian influenza virus HA and fowl adenovirus fiber2 and optimize the folding of fusion protein molecules; it can induce poultries to produce high-level specific antibodies to protect poultry from avian influenza and fowl adenovirus infection.

The fusion antigen contained in the vaccine of the disclosure is prepared by genetic engineering fermentation, which has the advantages of low cost, high antigen purity, good immunogenicity and high safety.

The above examples are preferred embodiments of the disclosure, but the embodiments of the disclosure are not limited by the above examples. Any other changes, modifications, substitutions, combinations and simplifications made without departing from the spiritual essence and principle of the disclosure shall be equivalent replacement methods, and are all included within the protective scope of the disclosure.

We claim:
1. An avian influenza and fowl adenovirus type 4 bi-combined genetic engineering subunit vaccine, wherein an antigen in the vaccine is a fusion antigen; the fusion antigen has:
   a) an avian influenza virus HA protein;
   b) a fowl adenovirus fiber2 protein;
   c) a specific linker peptide located between the avian influenza virus HA protein and the fowl adenovirus fiber2 protein; the amino acid sequence of the specific linker peptide is as shown in SEQ ID NO: 2.

2. The subunit vaccine according to claim 1, wherein the amino acid sequence of the fusion antigen is as shown in SEQ ID NO: 3.

3. The subunit vaccine according to claim 1, wherein the content of the fusion antigen in the vaccine is not less than 75 μg/ml.

4. The subunit vaccine according to claim 1, wherein the vaccine is formed by mixing and emulsifying an oil phase and a water phase; the water phase contains the fusion antigen.

5. A method for preparing the avian influenza and fowl adenovirus type 4 bi-combined genetic engineering subunit vaccine according to claim 1, wherein the vaccine is obtained by mixing and emulsifying the water phase containing the fusion antigen and the oil phase.

6. The method for preparing the subunit vaccine according to claim 5, wherein the method for preparing the fusion antigen comprises:
   Step 1: synthesizing a fusion expression gene sequence to construct a recombinant expression vector; synthesizing a fusion gene sequence shown in SEQ ID NO:1, and adding restriction enzyme sites ECOR I and NOT I at two ends of the fusion gene sequence, and meanwhile carrying out double digestion on a *Pichia pastoris* expression vector pPic9k using the restriction enzymes ECOR I and NOT I to obtain a fragment with a size of 9263 bp, and linking the synthesized fusion gene sequence with the *Pichia pastoris* expression vector pPic9k fragment recovered via double digestion using T4 DNA ligase to obtain a ligation product;
   Step 2: transforming the ligation product in step 1 into *E. coli* DH5α, picking colonies, carrying out positive cloning verification using PCR, and carrying out sequencing verification on a target fragment;
   Step 3: after sequencing in step 2 succeeds, extracting plasmids from the colonies to obtain recombinant plasmids, introducing the recombinant plasmids into *Pichia pastoris* GS11 using an electrotransformation method to obtain thallus;
   Step 4: collecting the thallus in step 3 and picking transformants capable of normally growing on a resistance plate, extracting genomes from the transformants, and carrying out PCR amplification on the target fragment;
   Step 5: after the target fragment is determined, activating the transformants again, and carrying out fermentation induction culture to obtain a protein solution containing the fusion antigen; and
   Step 6: purifying and precipitating the protein solution to obtain the fusion antigen.

7. The method for preparing the subunit vaccine according to claim 6, wherein the Step 2 is specifically as follows: the ligation product in Step 1 is transformed into *E. coli* DH5 α, 100 μl of *E. coli* DH5α cells molten on ice is put into a 5 ml EP tube with a round bottom, the ligation product in step 1 is added, the resulting mixture is put for 30 s on ice, subjected to heat shock for 45 s at 42° C., and then put on ice for 1-2 min, an soc culture medium is added until the final volume is 1 ml, the resulting mixture is subjected to shaking culture at 37° C. for 1 h, and a proper amount of cultured product is coated on an LB agar plate and cultured overnight at 37° C.; colonies are picked to be subjected to positive cloning verification using PCR, and sequencing verification is performed on the target fragment;
   the Step 3 is specifically as follows: after sequencing succeeds, plasmids are extracted from the colonies to obtain the recombinant plasmids, the recombinant plasmids are introduced into *Pichia pastoris* GS11 by using an electrotransformation method, wherein the electrotransformation conditions are as follows: the prepared recombinant plasmids are added into a 1.5 mL centrifuge tube containing 80 μL of *Pichia pastoris* GS115 competent cells to be subjected to ice bath for 15 min to obtain a plasmid competent mixed solution, the sucked plasmid competent mixed solution is added into a pre-cooled 0.2 cm electroconversion cup and the cup is subjected to electric shock transformation on an electromotor; electric shock is performed for 4.5 ms at 1500 V; after electric shock is completed, 500 μL of 1M pre-cooled sorbitol solution is added immediately and evenly mixed, the resulting mixed solution is transferred into a 1.5 mL centrifuge tube, and cultured for 2 h in a constant temperature shaker at 30° C. at 180 rpm; the resuscitated bacterial solution was centrifuged at a low speed for 5 min and 150-200 μL of suspended thallus is retained and coated on an YPD plate containing 1 M sorbitol and cultured for 48 h in a constant temperature incubator at 30° C.

8. The method for preparing the subunit vaccine according to claim 6, wherein the step 4 is specifically as follows: the thallus on the YPD plate in step 3 are collected and diluted into corresponding folds, 150-200 μL of bacterial solution is sucked to the YPD culture medium containing 0.4 g/ml G418 antibiotics, and statically cultured in a 30° C. constant temperature incubator for 2-4 days, transformants that can grow normally on the resistance plate are picked to extract the transformant genome, and PCR amplification is performed on the target fragment.

9. The method for preparing the subunit vaccine according to claim 6, wherein the step 5 is specifically as follows: the verified transformants are picked and inoculated in a BMGY culture solution to be subjected to shaking culture for 48 h at 30° C., then the cultured product is centrifuged under a low temperature at 4000 rpm for 10 min to remove the supernatant, then the BMMY culture solution are added to suspend the thallus, then the thallus is induced for 72 h with addition of methanol every 24 h; the culture solution was centrifuged under a low temperature at 4000 rpm for 10 min, and the supernatant is collected to obtain a protein solution, and SDS-PAGE identification is performed on the protein solution;
   the step 6 is specifically as follows: absolute ethanol whose volume is as twice as that of protein solution is added overnight for settlement, the solution after settlement is centrifuged under a low temperature at 8000 rpm/min for 5 min to remove the supernatant, and the avian influenza H9 subtype HA and adenovirus type 4 fiber2 fusion antigen is collected and precipitated.

10. The method for preparing the subunit vaccine according to claim 5, wherein the emulsifier used in the oil phase is span-80 and the solvent is white oil;

the emulsifier used in the water phase is Tween 80 and the solvent is water.

* * * * *

SEQUENCE LISTING

<160> NUMBER OF SEQ ID NOS: 4

<210> SEQ ID NO 1
<211> LENGTH: 3189
<212> TYPE: DNA
<213> ORGANISM: Artificial Sequence
<220> FEATURE:
<223> OTHER INFORMATION: fusion gene for constructing a recombinant
      expression vector, fully synthetic

<400> SEQUENCE: 1

```
atggaagtag tatcactaat aactatacta ctagtagcaa cagtaagcaa tgcagataaa        60
atctgcatcg gctatcaatc aacaaactcc acagaaactg tggacacact aacagaaaac       120
aatgtccctg tgacacatgc caaagaactg ctccacacag agcataatgg gatgctgtgt       180
gcaacaagct tgggacaacc tcttatttta gacacctgca ccattgaagg gctaatctat       240
ggcaatcctt cttgtgatct atcgctggaa ggaagagaat ggtcctatat cgtcgagaga       300
ccatcagctg tcaacggatt gtgttacccc gggaatgtag aaaatctaga agagctaagg       360
tcacttttta gttctgctag gtcttatcaa agaatccaga ttttcccaga cacaatctgg       420
aatgtgtctt acgatgggac aagcacagca tgctcaggtt cattctacag aagcatgaga       480
tggttgactc gaaagaacgg cgattaccct gtccaagacg cccaatacac aaataatcaa       540
gggaagaaca ttctttttcat gtggggcata aatcacccac ccaccgatac tacgcagaga       600
aatctgtaca cgagaaacga cacaacaacg agtgtggcaa cagaagaaat aaataggatc       660
ttcaaaccat tgataggacc aaggcctctt gtcaacggtt tgatgggaag aattgattat       720
tattggtctg tattgagacc gagtcaaaca ctgcgaataa aatctgatgg aatctaata       780 gctccatggt atggacacat tctttcagga gagagccacg gaagaattct gaagactgat       840
ttaaaaaggg gtagctgcac agtgcaatgt cagacagaga aggtggctt aaacacaaca       900 ctgccattcc aaaatgtaag taagtatgca tttggaaact gctcaaaata cattggcata       960
aagagtctca aacttgcagt tggtctgagg aatgtgcctt ctagatctag tagaggacta      1020 ttcgggggcca tagcagggt tatagaggga ggttggtcag ggctagttgc tggttggtat      1080
gggttccagc attcaaatga ccaagggtt ggtatggcag cagatagaga ctcaaccaa       1140 aaggcaattg ataaataac atccaaagtg aataatatag tcgacaaaat gaacaagcag      1200
tatgaagtca ttgatcatga attcagtgag gtagaaacta gacttaacat gatcaataat      1260
aagattgatg atcaaatcca ggatatatgg gcatataatg cagaattgct agttctgctt      1320
gaaaaccaga aaacactcga tgagcatgac gcaaatgtaa acaatctata taataaagta      1380
aagagggcgt tgggttccaa cgcggtgaa gatgggaaag atgtttcga gctataccac      1440 aaatgtgatg accaatgcat ggagacaatt cgaaacggga cctacaacag aaggaagtat      1500
```

```
caagaggagt caaaattaga aagacagaaa atagagggg tcaagctgga atctgaagga      1560
acttacaaaa tcctcaccat ttattcgact gttgcctcat ctcttgtgat tgcaatgggg      1620
tttgctgcct tcttgttctg ggccatgtcc aatgggtctt gcagatgcaa catttgtata      1680
taacctgaag tcctgcctcc tctgcctaag aatctagaa tttccgaagg tgaagctgtc       1740
gtcgtcggta tgctccgggc ccctaaaaga agacattccg aaaacgggaa gcccgagacc      1800
gaagcgggac cttccccggc tccaatcaag cgcgccaaac gcatggtgag agcatcccag      1860
cttgacctgg tttatccttt cgattacgtg gccgaccccg tcggagggct caacccgcct      1920
tttttgggag gctcaggacc cctagtggac cagggcggac agcttacgct caacgtcacc      1980
gatcccatca tcatcaagaa cagatcggtg gacttggccc acgaccccag tctcgatgtc      2040
aacgcccaag tcaactggc ggtggccgtt gaccccgaag gggccctgga catcaccccc       2100
gatggactgg acgtcaaggt cgacggagtg accgtaatgg tcaacgatga ctgggaactg      2160
gccgtaaaag tcgacccgtc cggcggattg gattccaccg cgggtggact ggggggtcagc    2220
gtggacgaca ccttgctcgt ggatcaggga gaactgggcg tacacctcaa ccaacaagga     2280
cccatcactg ccgatagcag tggtatcgac ctcgagatca atcctaacat gttcacggtc     2340
aacacctcga ccggaagcgg agtgctgaa ctcaacctaa agcgcaggg aggcatccaa        2400
gccgccagtt cgggagtggg cgtttccgtg gatgaaagcc tacagattgt caacaacact     2460
ctggaagtga aaccggatcc cagcggaccc cttacggtct ccgccaatgg cctagggctg     2520
aagtacgaca ctaataccct agcggtgacc gcgggcgctt taaccgtggt cggagggggg     2580
agcgtctcca cacccatcgc tacttttgtc tcgggaagtc ccagcctcaa cacctacaat     2640
gccacgaccg tcaattccag cgcgaacgcc ttctcttgcg cctactacct tcaacagtgg     2700
aacatacagg ggctccttgt tacctccctc tacttgaaat tggacagcgc caccatgggg     2760
aatcgccctg gggacctcaa ctccgccaat gccaaatggt tcaccttttg ggtgtccgcc     2820
tatctccagc aatgcaaccc ctccgggatt caagcgggaa cggtcagccc ctccaccgcc    2880
accctcacgg actttgaacc catggccaat aggagcgtga ccagcccatg acgtactcg      2940
gccaatggat actatgaacc atccatcggg gaattccaag tgttcagccc ggtggtaaca     3000
ggtgcctgga acccgggaaa catagggatc cgcgtcctcc ccgtgccggt ttcggcctcc    3060
ggagagcgat acacccttct atgctatagt ctgcagtgca cgaacgcgag cattttttaat    3120
ccaaacaaca gcggaaccat gatcgtggga cccgtgctct acagctgtcc agcggcctcc    3180
ctcccgtaa                                                            3189
```

<210> SEQ ID NO 2
<211> LENGTH: 22
<212> TYPE: PRT
<213> ORGANISM: Artificial Sequence
<220> FEATURE:
<223> OTHER INFORMATION: specific linker peptide located between the
      avian influenza virus HA protein and the fowl adenovirus fiber2
      protein, fully synthetic

<400> SEQUENCE: 2

Pro Glu Val Leu Pro Pro Leu Pro Lys Glu Ser Arg Ile Ser Glu Gly
1               5                   10                  15

Glu Ala Val Val Val Gly
            20

<210> SEQ ID NO 3
<211> LENGTH: 1061

```
<212> TYPE: PRT
<213> ORGANISM: Artificial Sequence
<220> FEATURE:
<223> OTHER INFORMATION: amino acid sequence of the fusion antigen,
      having: a) an avian influenza virus HA protein; b) a fowl
      adenovirus fiber2 protein; c) a specific linker; fully synthetic

<400> SEQUENCE: 3

Met Glu Val Val Ser Leu Ile Thr Ile Leu Leu Val Ala Thr Val Ser
1               5                   10                  15

Asn Ala Asp Lys Ile Cys Ile Gly Tyr Gln Ser Thr Asn Ser Thr Glu
            20                  25                  30

Thr Val Asp Thr Leu Thr Glu Asn Asn Val Pro Val Thr His Ala Lys
        35                  40                  45

Glu Leu Leu His Thr Glu His Asn Gly Met Leu Cys Ala Thr Ser Leu
    50                  55                  60

Gly Gln Pro Leu Ile Leu Asp Thr Cys Thr Ile Glu Gly Leu Ile Tyr
65                  70                  75                  80

Gly Asn Pro Ser Cys Asp Leu Ser Leu Glu Gly Arg Glu Trp Ser Tyr
                85                  90                  95

Ile Val Glu Arg Pro Ser Ala Val Asn Gly Leu Cys Tyr Pro Gly Asn
            100                 105                 110

Val Glu Asn Leu Glu Glu Leu Arg Ser Leu Phe Ser Ser Ala Arg Ser
        115                 120                 125

Tyr Gln Arg Ile Gln Ile Phe Pro Asp Thr Ile Trp Asn Val Ser Tyr
    130                 135                 140

Asp Gly Thr Ser Thr Ala Cys Ser Gly Ser Phe Tyr Arg Ser Met Arg
145                 150                 155                 160

Trp Leu Thr Arg Lys Asn Gly Asp Tyr Pro Val Gln Asp Ala Gln Tyr
                165                 170                 175

Thr Asn Asn Gln Gly Lys Asn Ile Leu Phe Met Trp Gly Ile Asn His
            180                 185                 190

Pro Pro Thr Asp Thr Thr Gln Arg Asn Leu Tyr Thr Arg Asn Asp Thr
        195                 200                 205

Thr Thr Ser Val Ala Thr Glu Glu Ile Asn Arg Ile Phe Lys Pro Leu
    210                 215                 220

Ile Gly Pro Arg Pro Leu Val Asn Gly Leu Met Gly Arg Ile Asp Tyr
225                 230                 235                 240

Tyr Trp Ser Val Leu Arg Pro Ser Gln Thr Leu Arg Ile Lys Ser Asp
                245                 250                 255

Gly Asn Leu Ile Ala Pro Trp Tyr Gly His Ile Leu Ser Gly Glu Ser
            260                 265                 270

His Gly Arg Ile Leu Lys Thr Asp Leu Lys Arg Gly Ser Cys Thr Val
        275                 280                 285

Gln Cys Gln Thr Glu Lys Gly Gly Leu Asn Thr Thr Leu Pro Phe Gln
    290                 295                 300

Asn Val Ser Lys Tyr Ala Phe Gly Asn Cys Ser Lys Tyr Ile Gly Ile
305                 310                 315                 320

Lys Ser Leu Lys Leu Ala Val Gly Leu Arg Asn Val Pro Ser Arg Ser
                325                 330                 335

Ser Arg Gly Leu Phe Gly Ala Ile Ala Gly Phe Ile Glu Gly Gly Trp
            340                 345                 350

Ser Gly Leu Val Ala Gly Trp Tyr Gly Phe Gln His Ser Asn Asp Gln
        355                 360                 365

Gly Val Gly Met Ala Ala Asp Arg Asp Ser Thr Gln Lys Ala Ile Asp
```

```
                370                 375                 380
Lys Ile Thr Ser Lys Val Asn Asn Ile Val Asp Lys Met Asn Lys Gln
385                 390                 395                 400

Tyr Glu Val Ile Asp His Glu Phe Ser Glu Val Glu Thr Arg Leu Asn
                405                 410                 415

Met Ile Asn Asn Lys Ile Asp Asp Gln Ile Gln Asp Ile Trp Ala Tyr
            420                 425                 430

Asn Ala Glu Leu Leu Val Leu Leu Glu Asn Gln Lys Thr Leu Asp Glu
            435                 440                 445

His Asp Ala Asn Val Asn Asn Leu Tyr Asn Lys Val Lys Arg Ala Leu
            450                 455                 460

Gly Ser Asn Ala Val Glu Asp Gly Lys Gly Cys Phe Glu Leu Tyr His
465                 470                 475                 480

Lys Cys Asp Asp Gln Cys Met Glu Thr Ile Arg Asn Gly Thr Tyr Asn
                485                 490                 495

Arg Arg Lys Tyr Gln Glu Glu Ser Lys Leu Glu Arg Gln Lys Ile Glu
                500                 505                 510

Gly Val Lys Leu Glu Ser Glu Gly Thr Tyr Lys Ile Leu Thr Ile Tyr
            515                 520                 525

Ser Thr Val Ala Ser Ser Leu Val Ile Ala Met Gly Phe Ala Ala Phe
            530                 535                 540

Leu Phe Trp Ala Met Ser Asn Gly Ser Cys Arg Cys Asn Ile Cys Ile
545                 550                 555                 560

Pro Glu Val Leu Pro Leu Pro Lys Glu Ser Arg Ile Ser Glu Gly
                565                 570                 575

Glu Ala Val Val Val Gly Met Leu Arg Ala Pro Lys Arg Arg His Ser
            580                 585                 590

Glu Asn Gly Lys Pro Glu Thr Glu Ala Gly Pro Ser Pro Ala Pro Ile
            595                 600                 605

Lys Arg Ala Lys Arg Met Val Arg Ala Ser Gln Leu Asp Leu Val Tyr
            610                 615                 620

Pro Phe Asp Tyr Val Ala Asp Pro Val Gly Gly Leu Asn Pro Pro Phe
625                 630                 635                 640

Leu Gly Gly Ser Gly Pro Leu Val Asp Gln Gly Gln Leu Thr Leu
                645                 650                 655

Asn Val Thr Asp Pro Ile Ile Ile Lys Asn Arg Ser Val Asp Leu Ala
                660                 665                 670

His Asp Pro Ser Leu Asp Val Asn Ala Gln Gly Gln Leu Ala Val Ala
            675                 680                 685

Val Asp Pro Glu Gly Ala Leu Asp Ile Thr Pro Asp Gly Leu Asp Val
            690                 695                 700

Lys Val Asp Gly Val Thr Val Met Val Asn Asp Trp Glu Leu Ala
705                 710                 715                 720

Val Lys Val Asp Pro Ser Gly Gly Leu Asp Ser Thr Ala Gly Leu
                725                 730                 735

Gly Val Ser Val Asp Asp Thr Leu Leu Val Asp Gln Gly Glu Leu Gly
            740                 745                 750

Val His Leu Asn Gln Gln Gly Pro Ile Thr Ala Asp Ser Ser Gly Ile
            755                 760                 765

Asp Leu Glu Ile Asn Pro Asn Met Phe Thr Val Asn Thr Ser Thr Gly
            770                 775                 780

Ser Gly Val Leu Glu Leu Asn Leu Lys Ala Gln Gly Gly Ile Gln Ala
785                 790                 795                 800
```

Ala Ser Ser Gly Val Gly Val Ser Val Asp Glu Ser Leu Gln Ile Val
            805                 810                 815

Asn Asn Thr Leu Glu Val Lys Pro Asp Pro Ser Gly Pro Leu Thr Val
            820                 825                 830

Ser Ala Asn Gly Leu Gly Leu Lys Tyr Asp Thr Asn Thr Leu Ala Val
            835                 840                 845

Thr Ala Gly Ala Leu Thr Val Val Gly Gly Ser Val Ser Thr Pro
            850                 855                 860

Ile Ala Thr Phe Val Ser Gly Ser Pro Ser Leu Asn Thr Tyr Asn Ala
865                 870                 875                 880

Thr Thr Val Asn Ser Ser Ala Asn Ala Phe Ser Cys Ala Tyr Tyr Leu
            885                 890                 895

Gln Gln Trp Asn Ile Gln Gly Leu Leu Val Thr Ser Leu Tyr Leu Lys
            900                 905                 910

Leu Asp Ser Ala Thr Met Gly Asn Arg Pro Gly Asp Leu Asn Ser Ala
            915                 920                 925

Asn Ala Lys Trp Phe Thr Phe Trp Val Ser Ala Tyr Leu Gln Gln Cys
930                 935                 940

Asn Pro Ser Gly Ile Gln Ala Gly Thr Val Ser Pro Ser Thr Ala Thr
945                 950                 955                 960

Leu Thr Asp Phe Glu Pro Met Ala Asn Arg Ser Val Thr Ser Pro Trp
            965                 970                 975

Thr Tyr Ser Ala Asn Gly Tyr Tyr Glu Pro Ser Ile Gly Glu Phe Gln
            980                 985                 990

Val Phe Ser Pro Val Val Thr Gly Ala Trp Asn Pro Gly Asn Ile Gly
            995                 1000                1005

Ile Arg Val Leu Pro Val Pro Val Ser Ala Ser Gly Glu Arg Tyr
            1010                1015                1020

Thr Leu Leu Cys Tyr Ser Leu Gln Cys Thr Asn Ala Ser Ile Phe
            1025                1030                1035

Asn Pro Asn Asn Ser Gly Thr Met Ile Val Gly Pro Val Leu Tyr
            1040                1045                1050

Ser Cys Pro Ala Ala Ser Leu Pro
            1055                1060

<210> SEQ ID NO 4
<211> LENGTH: 65
<212> TYPE: DNA
<213> ORGANISM: Artificial Sequence
<220> FEATURE:
<223> OTHER INFORMATION: gene for encoding a specific linker peptide
      fragment, fully synthetic

<400> SEQUENCE: 4
cctgaagtcc tgcctcctct gcctaaggaa tctagaattt ccgaaggtga agctgtcgtc    60
gtcgg    65